United States Patent
Cheng et al.

(10) Patent No.: US 9,335,321 B2
(45) Date of Patent: May 10, 2016

(54) METHOD FOR SCREENING AGENT WITH ANGIOGENIC-MODULATING ACTIVITIES USING TELEOST EMBRYO

(75) Inventors: Shuk Han Cheng, Hong Kong (CN); Po Kwok Chan, Hong Kong (CN)

(73) Assignee: CITY UNIVERSITY OF HONG KONG, Kowloon, Hong Kong (CN)

( * ) Notice: Subject to any disclaimer, the term of this patent is extended or adjusted under 35 U.S.C. 154(b) by 133 days.

(21) Appl. No.: 12/302,732

(22) PCT Filed: Jan. 8, 2007

(86) PCT No.: PCT/CN2007/000034
§ 371 (c)(1),
(2), (4) Date: Mar. 10, 2009

(87) PCT Pub. No.: WO2008/086645
PCT Pub. Date: Jul. 24, 2008

(65) Prior Publication Data
US 2009/0232742 A1    Sep. 17, 2009

(51) Int. Cl.
*G01N 33/50* (2006.01)

(52) U.S. Cl.
CPC ........ *G01N 33/5014* (2013.01); *G01N 33/5088* (2013.01); *G01N 2333/4603* (2013.01); *G01N 2333/515* (2013.01)

(58) Field of Classification Search
CPC .................................................. A01K 2267/03
USPC .......................................................... 800/14
See application file for complete search history.

(56) References Cited

U.S. PATENT DOCUMENTS

2002/0025297 A1* 2/2002 Serbedzija et al. ............ 424/9.2

FOREIGN PATENT DOCUMENTS

CN         1866025     11/2006
WO      WO 99/42606    8/1999

OTHER PUBLICATIONS

Slikker and Sabotka et al 1996, Annals of the New York Academy of Sciences, Current and Future Approaches to Neurotoxicity and Risk Assessment, 406-418.*
Kelloff, Cancer Epidemiology, 4:1-10,1995.*
Weinstein, B.M., "Plumbing the mysteries of vascular development using zebrafish," Cell & Development Biology (2002) vol. 13, pp. 515-522.
Zhang, L., et. al., "The effect of exogenous retinoic acid on the cardiovascular development of zebrafish embryos," ACTA Laboratorium Animalis Scientia Sinica, (Jun. 2006), vol. 14(2), pp. 84-88 [English-language abstract provided herewith], Abstract only.
Parng, C. et al., "Zebrafish: A preclinical model for drug screening," Assay and Drug Development Technologies (2002), vol. 1:1, pp. 41-48.
Kidd K. et al., "Fishing for novel angiogenic therapies," British Journal of Pharmacology (2003), vol. 140:4, pp. 585-594.
Lawson, N. et al., "In vivo imaging of embryonic vascular development using transgenic zebrafish," Developmental Biology (2002), vol. 248:2, pp. 307-318.
White R. E., "High-thoughput screening in drug metabolism and pharmacokinetic support of drug discovery" Anual Review of Pharmacology and Toxicology (2000), vol. 40, pp. 133-157.
Wikipedia website internet article Dec. 4, 2006, URL:http/en.wikipedia.org/w/index/php?title=High-throughput_ screening&oldid=92091908, 3 pages. [retrived on Dec. 4, 2009].
Supplementary European Search Report and Opinion from related EP Application No. 07701966.
International Preliminary Report on Patentability from International Patent Application No. PCT/CN2007/000034.
Cross, L. et al., "Rapid Analysis of Angiogenisis Drugs in a Live Fluorescent Zebrafish Assay," 2003, Arterioscler. Thromb. Vasc, Biol., 23, 911-912.
Epstein, F.H. et al., "A Perspective on the Value of Aquatic Models in Biomedical Research," 2005, Exp. Biol. Med. (Maywood) 230, 1-7.
Goldsmith, P., "Zebrafish as a Pharmacological Tool: The How, Why and When," 2004, Curr. Opin. Pharmacol., 4, 504-512.
Hallare, A. et al., "Comparative Embryotoxicity and Proteotoxicity of Three Carrier Solvents to Zebrafish (*Danio rerio*) Embryos," 2006, Ecotoxicol. Environ. Saf. 63, 378-388.
Hasan, J. et al., "Quantitative Angiogenesis Assays in Vivo—A Review," 2004, Angiogenesis 7, 1-16.
Liekens, S. et al., "Angiogenesis: Regulators and Clinical Applications," 2001, Biochem. Pharmacol. 61, 253-270.
Risau, W., Mechanisms of Angiogenesis, 1997, Nature 386, 671-674.
Serbedzija, G.N. et al., "Zebrafish Angiogenesis: A New Model for Drug Screening," 1999, Angiogenesis 3, 353-359.
Staton, C.A. et al., "Current MEthods for Assaying Angiogenesis in Vitro and in Vivo," 2004, Int. J. Exp. Pathol. 85, 233-248.
Taraboletti, G. et al., "Modelling Approaches for Angiogenesis," 2004 Eur. J. Cancer 40, 881-889.
Westerfield, M., The Zebrafish Book: A Guide for the Laboratory Use of Zebrafish, 1995, Eugene, OR, Univ. of Oregon Press (Table of Contents Only).

* cited by examiner

*Primary Examiner* — Valarie Bertoglio
(74) *Attorney, Agent, or Firm* — Kenyon & Kenyon LLP

(57) ABSTRACT

This invention relates to a method of 3-tier system for screening compounds, herb extract or extract of herb combination in formula with angiogenic-modulating activities using transparent teleost embryos as model.

24 Claims, No Drawings

METHOD FOR SCREENING AGENT WITH ANGIOGENIC-MODULATING ACTIVITIES USING TELEOST EMBRYO

This application is a 371 of PCT/CN2007/000034 said PCT application filed on Jan. 8, 2007.

FIELD OF THE INVENTION

Angiogenesis is a physiological process of formation of new blood vessels from existing blood vessels (Risau, 1997). This process normally occurs in growth and development, and wound healing by restoring blood flow to tissues. However, loss of control in angiogenesis is a common factor in most important diseases such as cancer and rheumatoid arthritis (Liekens et al., 2001). These diseases may result from or progress when new blood vessels either grow excessively or insufficiently. Excessive angiogenesis occurs, for example, in cancer by abnormal production of excessive amounts of angiogenic growth factors in order to form new blood vessels for excessive demand of nutrient. On the other hands, insufficient angiogenesis occurs, for example, in coronary artery disease, causing tissue damage and death due to inadequate production of angiogenic growth factor for sufficient growth of blood vessels. Therefore, therapies aimed at treating the loss of the control in angiogenesis are actively pursued by pharmaceutical companies all over the world.

BACKGROUND OF THE INVENTION

Even though there is a huge potential market for angiogenesis-related therapeutics, it is difficult to find a suitable assay to assess the effect of angiogenesis response (Staton et al., 2004). The most widely used assays are in vitro assays in which new drugs are tested in endothelial cells cultured in plastic flasks. The drawback is that it is difficult to extrapolate the observation made in an in vitro assay to model the complex process of angiogenesis actually occurring in in vivo situations (Staton et al., 2004; Taraboletti and Giavazzi, 2004). On the other hand, in vivo assays using animal models, for example mice, are costly, time-consuming and difficult for quantification (Staton et al., 2004). Thus, multiple in vitro assays are commonly employed for the identification of lead compounds. The efficacy of lead compounds on angiogenesis are subsequently validated by more than one in vivo assay. However, quantification is still an important key parameter for angiogenesis assays. Criteria for an ideal quantitative angiogenesis assay (Hasan et al., 2004) are that the assay should:
1) provide quantitative measure of structure of newly formed blood vessels;
2) provide quantitative measure of functional characters of newly formed blood vessels;
3) be able to distinguish the newly formed and pre-existing blood vessels;
4) allow long-term study;
5) be cost-effective, rapid, easy to use, reproducible; and
6) not cause any tissue damage;

Up to now, none of the existing in vivo assays really meets these requirements (Hasan et al., 2004; Taraboletti and Giavazzi, 2004). It appears that an in vivo drug screening assay using zebrafish as model fulfill the criteria of an ideal quantitative angiogenesis assay. An in vivo zebrafish assay has the advantages and convenience of in vitro assays (high throughput comparing to in vitro assays) and in vivo assays (being an intact organism), and thus is capable to serve as bridge or filter between in vitro screening and subsequent in vivo validation (Epstein and Epstein, 2005; Goldsmith, 2004; Parng et al., 2002). An in vivo zebrafish assay would eliminate those lead compounds, due to the toxic effects, from the list identified from the in vitro assays before entering a more expensive phase of in vivo validation. An in vivo zebrafish assay has been demonstrated as a useful method for screening angiogenic drugs (reviewed by (Kidd and Weinstein, 2003)). For example, Serbedzija and his coworkers described a screening methodology which was based on the counting number of subintestinal blood vessels formed on the surface of the yolk on both side of the embryo (Serbedzija et al., 1999). Blood vessels were stained for endogenous alkaline phosphatase activity. Transgenic zebrafish lines with fluorescent blood vessels have been developed (Cross et al., 2003; Lawson and Weinstein, 2002) such that the imaging and analysis of angiogenesis can be greatly simplified. However, there is still no methodology describing fully the procedures and tools how zebrafish may be used as a quantitative tool for angiogenic drug discovery together with the corresponding toxicity test.

SUMMARY OF THE INVENTION

This invention relates to a 3-tier screening system using teleost embryos as a model to screen agents with angiogenesis modulating activities and with no apparent toxicity. The present 3-tier screening system fulfills the criteria for an ideal quantitative angiogenesis assay listed above and provides an effective screening assay system to identify angiogenic modulating agent with least toxicity. The screening system consists of 3 hierarchical tiers: 1) lead identification; 2) general toxicity test; 3) organ-specific toxicity test. The preferred model of the present invention is zebrafish or medaka embryos. The advantage of the present invention is that it can rapidly identify potential angiogenic modulating agents at the first tier and these potential angiogenic modulating agents then subject to the tier 2 and 3 safety tests respectively. Therefore, the final candidates of the lead agents which pass all the 3 tiers will have the desirable angiogenic activity with the least toxicity.

In the first tier, the object is to identify quickly any agent capable of inducing alteration in the vasculature pattern in teleosts. In this tier, embryos are treated by agents in wide range of concentration, covering 7 orders of magnitude. To visualize blood vessels in transparent embryos, color staining is applied to detect endogenous alkaline phosphatase activity predominantly in vascular endothelial cells. The pattern of intersegmental vessels is chosen as the target to be examined because the pattern is regular and the variation between individual is very little, making the interpretation of angiogenic effect much easier. The preferred stage of embryos to be examined is at least 72 hour-post fertilization (hpf). Any alteration in the pattern of intersegmental vessels in any concentration of the agent will conclude as the angiogenic modulating agent and the agent will proceed to next tier.

In second tier, the dose response relationship of the agent will be determined. The dose response relationship describes the change in the effects, i.e. death and malformation, caused by differing levels of concentrations of the agent. Studying dose response relationship is central to determine safe and hazardous levels for the agent under study. Dose response relationship is plotted as a graph, called dose response curve. The first point along the curve where a response, i.e. total effects inclusive death and malformation, above zero is reached is referred as the threshold concentration, or no observed adverse effect concentration (NOAEC). Above the threshold concentration, undesirable adverse effects, i.e. death and malformation, will still appear and the effect will be stronger as the concentration increases. Therefore, in this tier, the NOAEC of the agent on teleost is determined. The preferred stage of embryos to be examined is 24 or 48 hpf.

In the third tier, it will be determined whether the agent at the level of NOAEC, instead of gross abnormalities, will induce any adverse effect at the organ level and cellular level. Therefore, safety of an agent will be evaluated by mean of a cytotoxicity test, organ toxicity test and cardiotoxicity test. In addition, angiogenic modulating activity will be tested at NOAEC. In this tier, visualization of intersegmental vessels is by microangiography imaging technology in which fluorescent dye, e.g. fluorescent microbead or fluorescent dextrans, are injected into the blood circulation such that it will be diffused to all registered blood vessels by blood circulation. Alteration of intersegmental vessels will be an indicator for angiogenic modulating activity. Agent with any positive results in one of the test or negative results in angiogenic modulating activity will be discarded. Otherwise, it will be considered as safe with angiogenic modulating activity.

DETAIL DESCRIPTION OF THE INVENTION

The present invention provides methods for screening agents for angiogenic modulating activity.

A variety of agents, either synthetic or from natural sources, can be screened using the present invention. Agents can be small molecules in pure form or a crude extract of an herb or crude extracts of a combination of different herbs. Agents should be administered in soluble form, with a variety of carrier solvents, e.g. ethanol, DMSO. The maximum concentrations of these solvents at which no malformation is induced in zebrafish are reported (Hallare et al., 2006). For example, the level of DMSO and ethanol used in zebrafish embryo assay should be below 1.5% and 1% respectively. The agent should first be dissolved in the carrier solvent, if necessary. Then it is added to the embryo media containing 20 fertilized eggs or healthy embryos at desired concentration. The preferred starting time of addition is prior the onset of angiogenesis, i.e. 24 hpf. Any effect induced by the presence of administered agent will be observed after certain interval period of time, e.g., 24 hours or 48 hours or more. Egg collection, picking up fertilized eggs, and identification of healthy embryos are well known to those of ordinary skill in the art (Westerfield, 1995).

In the first tier, fertilized egg at 4 hpf are bathed in embryo medium containing various concentrations of agent to be tested with 10-fold increment in concentration. The total number of concentrations to be tested is seven. Therefore, the range of concentrations to be tested covers 7 orders of magnitude. After incubation for a certain time period (e.g. 96 hours), embryos are fixed and blood vessels are visualized by color staining which specifically stains endogenous alkaline phosphatase activity predominantly in vascular endothelial cells. The number of intersegmental vessels is counted in each individual embryo. The number of embryos exhibiting a decrease or increase in the number of intersegmental vessels is counted at each concentration. An agent at any concentration inducing alteration of the number of intersegmental vessels will be stated as a potential lead and passed to tier 2. Simultaneously, numbers of dead embryos are also counted at each concentration. This data will serve as preliminary range of concentrations to be tested in the following second tier.

In the second tier, occurrence of death and malformation is counted upon exposure of teleost to different concentrations of the potential lead agent identified in tier 1. The concentration range to be tested is preliminarily determined in the range-finding experiment in the first tier. Concentrations to be tested are chosen in equal placement. Percentage of death and malformation in each concentration is determined and plotted in a graph to show the dose response relationship. A dose response curve is fitted to all the data points and the concentration corresponding to the highest concentration at which there are no statistically significant increase in the percentage of adverse effects between exposed group and control group is determined as NOAEC. This concentration level will then be used in the third tier. If for any agent no NOAEC can be determined, it will be discarded from the testing.

The aim of the third tier is to find out any side effect of the agent at the concentration level not causing any gross adverse effects, such as death and malformation in teleost. Therefore, tests included in the third tier are cellular toxicity test, organ-specific toxicity test and cardiotoxicity test. In the cytotoxicity test, number of dead cells (apoptotic cells) is quantified by flow cytometry. By flow cytometry, one can analyze, in addition to amount of dead cells, the amount of cells in different stages of cell cycle in a large number of samples, like 300 teleosts in a single experiment. In organ-specific toxicity, morphology of an organ is studied by fluorescent in situ hybridization with an organ specific probe. The morphology of the organ is quantified by 3D reconstruction of the optical sections from confocal images. Any change in the size and shape of the organ may reveal the toxic effects induced by the agent tested. Cardiotoxicity tests whether the positive candidate is able to affect cardiac functions, such as cardiac output and cardiac rhythm. Cardiotoxicity is an important test because more and more drugs have been shown to exhibit side effects on the heart, even in rare occurrence, and needed to be withdrawn from market. Finally, the effect of angiogenic modulating activity of the positive candidate is evaluated at the NOAEC. The positive candidate that does not induce any cytotoxic, organ-specific toxic and cardiotoxic effects and exhibits angiogenic modulating activity at the NOAEC is said to pass the third tier and, thus, this screening bioassay.

EXAMPLES

1. Material and Methods a. Egg Collection

Zebrafish mate and spawn with the light on. In order to collect eggs, it is necessary to protect the eggs from being eaten by the adults. The egg collection box used is made of acrylic with a metal mesh mounted on top. This is then covered with plastic seaweed so that the adults will mate where the plastic seaweed is, and the eggs that are spawned will fall into the acrylic box. The eggs are to be protected from adult fish consumption with a metal mash. The collection box should be removed after 30 min duration of the light period. The eggs are then to be collected by pouring fish water from the collection box through a fish net. The eggs should be rinsed under running tap water for 30 seconds, then transferred into a 90-mm Petri dish with 15 ml of embryo medium (19.3 mM NaCl, 0.23 mM KCl, 0.13 mM $MgSO_4$-$7H_2O$, 0.2 mM $Ca(NO_3)_2$, 1.67 mM Hepes (pH 7.2)). The dish should then be kept in an incubator at 28° C.

b. Administration of Agents

Agents are dissolved in a desired concentration such that the highest testing concentration contains a concentration of carrier solvent (e.g. DMSO, ethanol) not more than the recommended tolerant concentration. Agents are to be added directly to the medium solution at 4 hpf of the fish embryos. Assays should be performed in Petri dishes (60 mm×15 mm, Falcon, BD Bioscience, San Jose, Calif.). Each Petri dish is to hold 20 embryos.

As a primary screen for compound effects in tier 1, each agent is tested at 8 different concentrations, with 1 order of magnitude difference to determine which concentration will provide the most information. For a dose response study in tier 2, the range of concentrations to be tested covers from the lowest at which no adverse effect is observed to the highest concentration at which all embryos are killed.

For cytotoxicity, cardiotoxicity and organ toxicity in tier 2 and the mechanistic study in tier 3, the only concentration to be tested is the NOAEC determined from the dose response curve. For each concentration of the agent, 6 ml of culture medium is to be added to twenty embryos cultured in a Petri dish. Fifteen replications per agent per concentration (i.e. 20×15=300 embryos for each concentration of an agent) are then tested. The effect could be observed at different time points, e.g. 28 hpf, 52 hpf or 76 hpf. Furthermore, the further experiments to examine toxicity and angiogenesis can be performed following agent treatment.

c. Toxicity Test

To determine the toxicity of a compound for a biological system, an observable and well-defined endpoint must be identified. Mortality is one of these widely used endpoints. The index of lethal effects describing the potency of a compound is called $LC_{50}$, which is defined as the dosage of a chemical causing death in at least 50% of the animals tested. In addition to lethality, adverse effects such as malformation in morphology induced by a compound can be used as an observable endpoint. These adverse outcomes along with death are grouped as total adverse effects. The potency of a compound to induce adverse effects is defined as $EC_{50}$, which is the concentration of a compound causing at least 50% of the animals tested to exhibit abnormal appearances as well as death.

Mortality and total adverse effect were determined to be observable endpoint in the present study. After administering a compound to the fish embryos, the embryos are to be maintained at 28° C. until 28 hpf and 52 hpf, respectively. Twenty-four and forty-eight hours after adding the compound to the medium in which the fish embryos are cultured, the embryos are then visually inspected for mortality, movements and gross morphological defects under a dissecting microscope (Zeiss, Jena, Germany). The number of dead embryos of the 20 embryos tested in each experiment is then to be scored. Data collected from the 15 replicates are to be tested for the null hypothesis that no differences existed between mortality over all concentrations. Analyses of variance are then done, along with the post-hoc Tukey's honestly significant difference test to determine the differences in mortality between treatment concentrations and the untreated control. Likewise, analyses of variance and the post-hoc Tukey honest significant difference test are both used to determine the differences in total adverse effects between treatment concentrations and the untreated control. The software Statistica for Windows (StatSoft, Tulsa, Okla., USA) is to be used for the calculations.

d. Endogenous Alkaline Phosphatase Staining

Embryos older than 72 hpf can be used for endogenous alkaline phosphatase staining Specifically, embryos are fixed in 4% paraformaldehyde (PFA) in PBS and 1% Triton x-100. Embryos are fixed for overnight at 4° C. and then washed four times in PBS/0.1% Tween-20 (PBT) for 5 minutes. For staining, the embryos are equilibrated three times in a TMNT buffer (0.1M Tris-HCl pH 9.5; 50 mM $MgCl_2$; 0.1 M NaCl; 0.1% Tween 20) for 10 minutes at room temperature. After the embryos are equilibrated, they are stained in substrate solution (4.5 µl of 75 mg/ml nitro blue tetrazolium (NBT) and 3.5 µL of 50 mg/ml X-phosphate for 1 ml of TMNT solution).

After staining for 12 minutes, all the blood vessels in the fish embryo are labeled. The staining reaction is stopped by washing three times in PBT and embryos are fixed in 4% paraformaldehyde in PBS at room temperature for 30 minutes. The embryos are then washed briefly in PBT twice and 10 minutes 4 times. After washing, embryos should be immersed in 70% glycerol in PBS before examination and image capturing on a CCD camera.

To examine pro-/anti-angiogenic activity induced by a compound, the number of intersegmental vessels is required to be counted under a stereomicroscope or a compound microscope. Stained embryos are positioned laterally in glycerol. The region of examination is from the first intersegmental vessels to the one just above the anus. In general, there should be 12-13 pairs. The advantage is that there is a constant number of intersegmental vessels in 3-day embryos which makes the comparison between the control and treatment groups easier. Another advantage of using the zebrafish for this type of assay is that the subintestinal vessels, which are located over the yolk, are both sensitive to factors which affect vessel formation and are easily assayed by this method. The subintestinal vessels are normally present on the dorso-lateral surface of the yolk of zebrafish embryos by 48 hours of development. They form a distinct basket shape that extends 50-100 µm from the ventral edge of the somite over the yolk. By assaying the subintestinal vessels at 72 hours of development (24 hours after the subintestinal vessels normally appear), the normal variation in the timing of the vessel formation is avoided.

e. Microangiography

Procedures of microangiography are adopted from Weinstein et al. (Nat Genet, 1995), with modifications. Embryos are to be mounted laterally in 0.3% agarose as described below. Fluoresceinated and carboxylated latex microbeads (0.02-µm, cat# F-8787, Molecular Probes, USA) are then injected into the sinus venosus. The bead suspension should be diluted 1:1 with 2% BSA, sonicated at maximum power for 5 minutes, then centrifuged at maximum speed for 5 minutes. The supernatant is then to be transferred to a new tube for injection. Glass microneedles are then prepared from 1 mm OD capillaries (World Precision Instruments, cat # TW100-4 or TW100E-4 for glass without or with an internal filament) by using a Narishige PC-10 micropipette puller. To make these microneedles, this micropipette puller is required to pull the glass capillary vertically using the gravitational force of its own weight. A double pull is set in which the first pull is at a temperature of 76° C. and the second pull is at a temperature of 64° C. Microneedles are then to be broken open by a Narishige MF-900 micro-forge to give an opening of approximately 5 µm in width. The tip of microneedle needs to be broken by pushing against a small drop of glass melted on to the platinum wire of the micro-forge, monitored at 10× object of the micro-forge. No pipette holding is needed in this protocol since the embryos are mounted in agarose. The bead suspension is then loaded into a microneedle at the wider end with a micropipette loader. A glass microneedle is then inserted obliquely into the sinus venosus. Many (20+) small boluses of bead suspension should be injected over the course of up to a minute. Confocal images are acquired after letting the embryo recover for 3-5 minutes. The instrument setting is like the one described below. After injection, fluorescent beads will circulate around the whole vascular network, lighting up each blood vessel with active blood flow from the heart. Confocal images (Carl Zeiss confocal microscope equipped with LSM version 5) are then acquired for detailed reconstruction of the 3D structure of the zebrafish embryo vascular system.

Embryo prepared for microangiography should be immobilized by agarose. Agarose solution (0.3%) is prepared and kept at around 45° C. on a heat block. Embryos are to be transferred to a clean slide by using a Pasteur pipette with a broad opening. To avoid yolk sac damaging, a small drop of solution should be added to the embryo before addition of pre-heat 0.3% agarose to the embryo. With a 27 G needle, the embryo is arranged to the appropriated position just before the agarose hardens (it usually requires a minute or two).

To start with, a laser lamp with the appropriate wave length (e.g., 488 nm laser for FITC/fluorescein and acridine orange) should be switched on first. The pinhole size is then adjusted to a value, so that the airy value is 1.00. The "Find" button in the side menu bar is used to adjust detector gain, offset and amplifier gain automatically. Detector gain and amplifier gain, if necessary, are to be adjusted to enhance intensity and for the detector offset to suppress background noise. The position of starting optical section ("slice") is defined and marked by selecting "Mark first". Similarly, the position of ending optical section is defined and marked by selecting "Mark last". The interval and number of slice was defined by setting "X:Y:Z: =1:1:1" so that the resolution of the Z-axis is set as X and Y resolution. Series stack confocal images are then captured, saved, and recorded in CD-R for backup. Confocal images can be exported as TIFF (16-bit raw image) by using the standalone version of LSM image browser (Carl Zeiss) for analysis in other image analysis software, e.g. MetaMorph (Universal Imaging, USA).

f. Whole Mounted In Situ Hybridization

In addition to performing visual screens, specific molecular changes in teleost tissues can be detected by in situ hybridization of RNA or antibody staining of specific proteins. A digoxigenin-labeling kit from Roche can be used to label the antisense RNA probes. Antisense probes are synthesized by linearizing plasmids pBlueScript (10 µg) with appropriate restriction enzymes in a 50 µl cocktail. Agarose gel electrophoresis is to be used as a monitor to make sure the plasmid is totally digested, and an equal volume of phenol/chloroform (Gibco BRL, Life Technology, USA) is used to stop the reaction. The mixture is then centrifuged on a bench top microcentrifuge under room temperature for 3 minutes at full speed (13,000 rpm). The aqueous phase should be transferred to a new tube followed by the addition of 1/10 volumes of 3M sodium acetate (pH 8.0) (Sigma, USA) and 2 volumes of ethanol (Sigma, USA), centrifuged for 30 minutes at room temperature. The pellet is then washed with 70% ethanol and left to air dry on bench, resuspended in an appropriate amount of RNase-free (DEPC; Sigma, USA) water to a concentration of 0.5 µg/µl.

Linearized plasmids are then transcribed with T3 RNA polymerase or T7 RNA polymerase in a transcription cocktail, incubated for 2 hours at 37° C. for the preparation of non-radioactive digoxigenin transcripts. The reaction is to be stopped by adding 1 µl of EDTA (0.5M, pH8.0). The addition of 2.5 µl of LiCl (4M) and 75 µl of cold ethanol is done to precipitate the RNA probe by centrifuging at full speed for 30 minutes at 4° C. The pellet is then washed with 70% ethanol, left for air dry on bench and resuspended in RNase-free (DEPC) water.

Whole mount in situ hybridization can be carried out as described by Westerfield (1994) with modifications (Cheng et al. 2000): Embryos at 24 hpf are to be dechorionated by using a pair of forceps and fixed in PBS (phosphate-buffered saline) with 4% paraformaldehyde (PFA) and 1% Triton X-100 at 4° C. overnight. Briefly, antisense RNA is then synthesized by linearising the plasmid and transcribing with T7 polymerase and Digoxigenin-11-UTP (Roche, Basel, Switzerland). The embryos should be transferred to methanol and stored at −20° C. to increase permeability. They are then washed and lightly digested with 10 µg/ml proteinase K in PBT (PBS with 0.1% Tween 20) before incubating with the antisense probes in situ hybridization solution (50% formamide, 5×SSC, 50 µg/ml Heparin, 500 µg/ml tRNA, 9 mM citric acid, pH 6.0, and 0.1% Tween 20) at 65-70° C. overnight. Following hybridization, probes are removed with high-stringency washes. In brief, embryos are washed twice in 50% Formamide: 50% (2×SSC/0.1%). Tween-20), each for 30 minutes, followed by 2×SSC/0.1% Tween-20 at 65° C. for 15 minutes, 2×SSC and 0.2× SSC each twice for 30 min, at 65° C. Embryos were subsequently incubated with pre-absorbed sheep anti-digoxigenin-alkaline phosphatase Fab fragments (Roche, Basel, Switzerland) on a nutator at 4° C. overnight. After washing 6 times in PBT, 5-bromo-4-chloroindolyl phosphate was added as substrate and nitro blue tetrazolium as coupler (Roche, Basel, Switzerland) for color staining.

g. Apoptosis

Embryos treated with agents (15 replicates) are pooled into a single 90-mm Petri dish coated with 0.3% agarose and washed three times in an embryo culture medium. Dechorionation is done under a stereomicroscope by using a pair of forceps to tear off the chorion. The embryos are then transferred to a 15-ml culture tube filled with 8-ml trypsin solution (0.5 mg/ml trypsin in a solution of 0.14M of NaCl, 0.05M of KCl, 0.005M of glucose, 0.007M of $NaHCO_3$ and 0.7 mM of EDTA). Then the embryos are to be triturated through a narrow bore Pasteur pipette until they are dissociated with continuous checking under a dissection microscope. The cell suspension is then centrifuged at 1000×g for 7 minutes at 4° C. The supernatant is discarded and cells are resuspended in 5 ml PBS to wash away the trypsin. They are then centrifuged again at 1000×g for 7 minutes at 4° C., followed by resuspension in 5 ml of PBS and centrifuged at 1000×g for 7 minutes at 4° C. The aqueous solution is discarded, and the pellet is then resuspended completely in 200 µl of PBS. Following this, 2 ml of 70% ethanol is added and the mixture is incubated at −20° C. overnight. The sample is then centrifuged at 1000×g for 7 minutes at 4° C. and pellet is added with 100 µl of propidium iodide (400 µg/ml) and 100 µl of RNase (1 mg/ml), incubated at 28.5° C. for 30 minutes before flow cytometry analysis.

h. Cardiotoxicity

Embryos prepared for microangiography should be immobilized by agarose. Agarose solution (0.3%) is prepared and kept at around 45° C. on a heat block. Embryos are to be transferred to a clean slide by using a Pasteur pipette with a broad opening. To avoid yolk sac damaging, a small drop of solution should be added to the embryo before addition of pre-heat 0.3% agarose to the embryo. With a 27 G needle, the embryo is arranged to their lateral position just before the agarose hardens. After agarose hardening, circulation at the tail region is examined under dissection microscope with CCD camera connected either to a personal computer equipped with video grabbing device or to digital video camera. In the case of digital video camera, data stored in mini-DV tape is transferred back to personal computer via i-Link connection and saved in AVI format for video image analysis. After video image analysis, data for the power spectrum of blood cell movement is obtained. Two parameters are derived from the power spectrum. The first parameter representing the heart rate is the basic frequency component which is the value of frequency with biggest power value. The second parameter is the ratio of the power value of the basic frequency component to the total power value of the whole spectrum. This ratio is correlated with the heart beat rhythmicity.

2. Results a. Tier 1

Totally, 1431 single compounds, 107 herbs singularly and 13 formulas had been screened in tier 1. These agents were chosen from books of Traditional Chinese Medicine. Out of 1431 compounds, there were 11 showing anti-angiogenic modulating activity at least in one of the tested concentrations. The phenomenon of anti-angiogenesis was the absence of at least one intersegmental vessel. Out of 107 herbs, there were 11 showing anti-angiogenic modulating activity at least in one of the tested concentrations. Out of 13 formulas tested, there were 4 showing anti-angiogenic modulating activity at least in one of the tested concentrations while there were 3 showing pro-angiogenic modulating activity at least in one of the tested concentrations. Same agents purchased from different supplier also exhibited similar responses.

b. Tier 2

Twenty nine agents passed the first tier and were tested in the second tier. General toxicity tests have been carried out. The NOAECs for each agent were then been determined. Among them, there were 6 agents (4 herbs and 2 formulas) that no NOAEC could be determined and thus they were not further tested in the third tier.

c. Tier 3

Toxicity testing at the NOAEC was carried out. All 11 compounds at their NOAECs induced ectopic apoptosis in teleost embryos and were failed in the cytotoxicity test. Therefore, they were failed in the third tier and no further toxicity test was carried out. Five out of 7 herbs induced ectopic apoptosis at their NOAECs while the remaining 2 passed the cytotoxicity test. Among these 2, only one exhibited antiangiogenic activity and passed organ-specific toxicity tests and cardiotoxicity at its NOAEC. Furthermore, 3 out of 5 formulas did not induce ectopic apoptosis at their NOAEC and proceeded to further tests while the remaining 2 failed in the cytotoxicity test. Among the 3 passing the cytotoxicity test, one failed to induce any change in vasculature at its NOAEC. But there was 1 exhibited anti-angiogenic activity at its NOAEC while there was 1 exhibited pro-angiogenic activity. These 2 formulas had passed the organ-specific toxicity tests and cardiotoxicity test. Therefore, there were 3 agents, including 1 herb and 2 formulas, that passed all 3 tiers tests.

REFERENCES

Cross, L. M., Cook, M. A., Lin, S., Chen, J. N. and Rubinstein, A. L. (2003). Rapid Analysis of Angiogenesis Drugs in a Live Fluorescent Zebrafish Assay. *Arterioscler. Thromb. Vasc. Biol.* 23, 911-912.

Epstein, F. H. and Epstein, J. A. (2005). A Perspective on the Value of Aquatic Models in Biomedical Research. *Exp. Biol. Med.* (Maywood) 230, 1-7.

Goldsmith, P. (2004). Zebrafish as a Pharmacological Tool: The how, Why and when. *Curr. Opin. Pharmacol.* 4, 504-512.

Hallare, A., Nagel, K., Kohler, H. R. and Triebskorn, R. (2006). Comparative Embryotoxicity and Proteotoxicity of Three Carrier Solvents to Zebrafish (*Danio Rerio*) Embryos. *Ecotoxicol. Environ. Saf* 63, 378-388.

Hasan, J., Shnyder, S. D., Bibby, M., Double, J. A., Bicknel, R. and Jayson, G. C. (2004). Quantitative Angiogenesis Assays in Vivo—a Review. *Angiogenesis* 7, 1-16.

Kidd, K. R. and Weinstein, B. M. (2003). Fishing for Novel Angiogenic Therapies. *Br. J. Pharmacol.* 140, 585-594.

Lawson, N. D. and Weinstein, B. M. (2002). In Vivo Imaging of Embryonic Vascular Development using Transgenic Zebrafish. *Dev. Biol.* 248, 307-318.

Liekens, S., De Clercq, E. and Neyts, J. (2001). Angiogenesis: Regulators and Clinical Applications. *Biochem. Pharmacol.* 61, 253-270.

Parng, C., Seng, W. L., Semino, C. and McGrath, P. (2002). Zebrafish: A Preclinical Model for Drug Screening. *Assay Drug Dev. Technol.* 1, 41-48.

Risau, W. (1997). Mechanisms of Angiogenesis. *Nature* 386, 671-674.

Serbedzija, G. N., Flynn, E. and Willett, C. E. (1999). Zebrafish Angiogenesis: A New Model for Drug Screening. *Angiogenesis* 3, 353-359.

Staton, C. A., Stribbling, S. M., Tazzyman, S., Hughes, R., Brown, N. J. and Lewis, C. E. (2004). Current Methods for Assaying Angiogenesis in Vitro and in Vivo. *Int. J. Exp. Pathol.* 85, 233-248.

Taraboletti, G. and Giavazzi, R. (2004). Modelling Approaches for Angiogenesis. *Eur. J. Cancer* 40, 881-889.

Westerfield, M. (1995). *The Zebrafish Book: A Guide for the Laboratory use of Zebrafish*. Eugene: Univ. of Oregon Press.

The claims are:

1. A biological method of screening an agent having angiogenic modulating activity, which is carried out by a hierarchical 3-tier biological screening assay system comprising:
   (i) in the first tier,
      (a) treating teleost embryos with a test agent at different concentrations covering seven orders of magnitude, while simultaneously, testing a control group
      (b) observing the vascular system of said embryos, wherein said embryos are at least 3-day old embryos, for any alteration in the constant number of intersegmental vessels at the different concentrations of the test agent;
   wherein any observed alteration in the constant number of intersegmental vessels in the teleost embryo treated with the test agent will lead to a conclusion that the test agent is an angiogenic modulating agent and the agent will proceed to the second tier for further testing;
   (ii) in the second tier,
      (a) plotting a dose response curve to show the dose response relationship of the test agent as compared to a control;
      (b) determining the highest concentration at which there are no statistically significant increases in the percentage of adverse effects on teleost embryos between the group exposed to the test agent and the control group, wherein said adverse effects include death or malformation of the teleost embryos;
   wherein said highest concentration is determined to be the no observed adverse effect concentration (NOAEC) and the test agent will proceed to the third tier for further testing;
   (iii) in the third tier,
      (a) determining whether the test agent at the level of NOAEC induces adverse effects at the organ level and cellular level in teleost embryos thereby resulting in an evaluation of the safety of said test agent, and
      (b) determining the parameters of the angiogenic modulating activity of said test agent at the level of NOAEC.

2. The method of claim 1, wherein in the first tier, the teleost embryos at 4 to 20 hours post fertilization are bathed in embryo medium containing different concentrations of the test agent for a determined period of time; in the second tier, the adverse effects of the test agent on the teleost embryos, such as death or malformation, are determined at different concentrations after at least a 24 hour exposure time; and in the third tier, alteration of intersegmental vessels is used as an indicator for angiogenic modulating activity.

3. The method of claim 1, wherein, in the first tier, the vascular system is observed by color staining to observe endogenous alkaline phosphatase activity in vascular endothelial cells, and in the third tier, the adverse effects at the organ level and cellular level are selected from the group consisting of determining: the amount of dead cells, the amount of cells in different stages of cell cycle, changes in the size and shape of an organ, cardiotoxicity including changes in cardiac output, cardiac rhythm, caudal circulation or any combination thereof to evaluate the safety of said agent.

4. The method of claim 1, wherein the teleost are zebrafish.

5. The method of claim 1, wherein in the first tier, the stage of embryos to be examined is at least 72 hour-post fertilization; and in the second tier, the stage of embryos to be examined is 24 or 48 hour-post fertilization.

6. The method of claim 1, wherein in the first tier the teleosts are observed between 3 to 5 days post fertilization.

7. The method of claim 1, wherein the vascular system is observed by staining endothelial cells with color substrates or fluorescent substrates in fixed teleosts.

8. The method of claim 1, wherein the vascular system is observed by injecting fluorescent substrates into the circulation system in live teleosts.

9. The method of claim 1, wherein the vascular system is observed by counting the number of intersegmental blood vessels, either totally from head to tail or in particular region, for example the caudal region.

10. The method of claim 1, wherein step (ii) comprises determining the adverse effects of the agents on teleosts at different concentrations after at least a 24 hour exposure time.

11. The method of claim 10, wherein the adverse effects include death and malformations.

12. The method of claim 11, wherein the malformations are observed as changes on the external morphology of teleost.

13. The method of claim 10, wherein the no observed adverse effect concentration (NOAEC) is calculated in the dose response relation between agents and adverse effects.

14. The method of claim 13, wherein test agent exposure is at least 24 hours.

15. The method of claim 1, wherein step (iii) (a) comprises measuring the three dimensional size and the shape of organs.

16. The method of claim 15, wherein the organs are visualized by organ-specific substrates.

17. The method of claim 16, wherein the organ-specific substrates are fluorescent.

18. The method of claim 15, wherein the three dimensional size and shape of the organs are determined quantitatively.

19. The method of claim 1, wherein in step (iii) adverse effects at the cellular level are determined by measuring the cellular toxicity of agents.

20. The method of claim 19, wherein cellular toxicity is determined in a at least 100 teleosts.

21. The method of claim 1, wherein step (iii)(a) comprises determining the cardiotoxicity of agents in the teleost embryos.

22. The method of claim 21, wherein the teleost embryos are at least 48 hour post fertilization.

23. The method of claim 21, wherein the cardiotoxicity parameters to be measured are heart rate and heart beat rhythmicity.

24. The method of claim 21, wherein the cardiotoxicity parameter to be measured is caudal circulation.

* * * * *